(12) United States Patent
Yoshioka et al.

(10) Patent No.: US 9,056,811 B2
(45) Date of Patent: Jun. 16, 2015

(54) METHOD FOR PRODUCING ALCOHOL BY GUERBET REACTION

(75) Inventors: Tetsuya Yoshioka, Tokyo (JP); Takashi Tsuchida, Tokyo (JP); Jun Kubo, Tokyo (JP); Shuji Sakuma, Tokyo (JP)

(73) Assignee: Kabushiki Kaisha Sangi, Tokyo (JP)

( * ) Notice: Subject to any disclaimer, the term of this patent is extended or adjusted under 35 U.S.C. 154(b) by 0 days.

(21) Appl. No.: 13/822,047

(22) PCT Filed: Sep. 14, 2011

(86) PCT No.: PCT/JP2011/005191
§ 371 (c)(1),
(2), (4) Date: Mar. 11, 2013

(87) PCT Pub. No.: WO2012/035772
PCT Pub. Date: Mar. 22, 2012

(65) Prior Publication Data
US 2013/0172634 A1  Jul. 4, 2013

(30) Foreign Application Priority Data
Sep. 15, 2010  (JP) ................ 2010-206803

(51) Int. Cl.
*C07C 29/34* (2006.01)
*C07C 31/10* (2006.01)
*C07C 31/12* (2006.01)
*C07C 31/125* (2006.01)
*B01J 21/10* (2006.01)
*B01J 23/00* (2006.01)
*B01J 27/18* (2006.01)
*B01J 29/08* (2006.01)
*B01J 37/03* (2006.01)

(52) U.S. Cl.
CPC ............ *C07C 29/34* (2013.01); *B01J 21/10* (2013.01); *B01J 23/007* (2013.01); *B01J 27/18* (2013.01); *B01J 29/082* (2013.01); *B01J 37/03* (2013.01)

(58) Field of Classification Search
None
See application file for complete search history.

(56) References Cited

U.S. PATENT DOCUMENTS

| | | | |
|---|---|---|---|
| 8,080,695 B2 * | 12/2011 | Tsuchida et al. | 568/902 |
| 8,232,433 B2 * | 7/2012 | Onda et al. | 568/902.2 |
| 8,603,201 B2 * | 12/2013 | Tsuchida et al. | 44/452 |
| 2003/0181769 A1 | 9/2003 | Both et al. | |
| 2003/0181770 A1 | 9/2003 | Both et al. | |
| 2007/0255079 A1 * | 11/2007 | Tsuchida et al. | 568/902.2 |
| 2009/0056204 A1 * | 3/2009 | Tsuchida et al. | 44/452 |

FOREIGN PATENT DOCUMENTS

| | | |
|---|---|---|
| JP | 05-017381 A | 1/1993 |
| JP | 09-227424 A | 9/1997 |
| JP | 2004-509156 A | 3/2004 |
| JP | 2004-523472 A | 5/2004 |
| JP | 2007-527938 A | 10/2007 |
| JP | 2008088140 | 4/2008 |
| JP | 2008-303160 A | 12/2008 |
| JP | 2009-029712 A | 2/2009 |
| JP | 2009-051760 A | 3/2009 |
| JP | 2009-167129 A | 7/2009 |
| JP | 2009-167183 A | 7/2009 |
| JP | 2009-173611 A | 8/2009 |
| JP | 2009-220105 A | 10/2009 |
| WO | 2005/085321 A1 | 9/2005 |
| WO | 2006/059729 A1 | 8/2006 |
| WO | WO 2011054483 A1 * | 5/2011 |

OTHER PUBLICATIONS

WO 2011054483 A1, May 2011, pp. 1-6; English translation.*
JP2008088140, Apr. 17, 2008, pp. 1-7; English translation.*
Carlini, C., et al., Guerbet condensation of methanol with n-propanol to isobutyl alcohol over heterogeneous bifunctional catalysts based on Mg—Al mixed oxides pertially substituted by different metal components, Journal of Molecular Catalysis A: Chemical, 2005, vol. 232, No. 1-2, pp. 13-20.
Koda, K., et al., Guerbet Reaction of Ethanol to n-Butanol Catalyzed by Iridum Complexes, Chemistry Letters, 2009, vol. 38, No. 8, pp. 838-839.
Yang, K., et al., One-step Synthesis of n-Butanol from Ethanol Condensation over Alumina-supported Metal Catalysts, Chinese Chemical Letters, 2004, vol. 15, No. 12, pp. 1497-1500.
Ueda, W., et al., Condensation of alcohol over solid-base catalyst to form higher alcohols, Catalysis Letters, 1992, vol. 12, No. 1-3, pp. 97-104.

* cited by examiner

*Primary Examiner* — Fereydoun G Sajjadi
*Assistant Examiner* — Medhanit Bahta
(74) *Attorney, Agent, or Firm* — Hodgson Russ LLP

(57) ABSTRACT

A method for increasing the yield of alcohols by a Guerbet reaction in a gas phase and reducing production cost is provided. A method for producing alcohols by a Guerbet reaction, wherein the reaction is performed in a gas phase and at a total pressure of less than 1 atm and preferably from 0.01 to 0.5 atm, using one or more raw material alcohols.

11 Claims, No Drawings

METHOD FOR PRODUCING ALCOHOL BY GUERBET REACTION

TECHNICAL FIELD

The present invention relates to alcohol production by a Guerbet reaction under reduced pressure and in a gas phase.

BACKGROUND ART

As a method for synthesizing alcohols, Guerbet reactions that synthesize alcohols dimerized by condensing two molecules of a raw material alcohol are known (see patent documents 1 to 12 (PTLs 1 to 12)). Many of these Guerbet reactions are a liquid phase reaction and are performed at normal pressure or in a pressurized state. In addition, in the case of performing the reactions in a gas phase, the reactions are normally performed at normal pressure. For example, patent document 8 discloses a reaction comprising bringing two or more raw material alcohol gases into contact with a hydroxyapatite (calcium hydroxyapatite) at normal pressure (paragraph [0036]), and patent document 12 discloses a reaction comprising bringing ethanol gas into contact with strontium phosphate apatite (strontium hydroxyapatite) at normal pressure (paragraph [0025]).

CITATION LIST

Patent Literature

PTL 1: Japanese Unexamined Patent Application Publication No. 05-17381
PTL 2: Japanese Unexamined Patent Application Publication No. 09-227424
PTL 3: Japanese Unexamined Patent Application Publication (Translation of PCT Application) No. 2004-509156
PTL 4: Japanese Unexamined Patent Application Publication (Translation of PCT Application) No. 2004-523472
PTL 5: Japanese Unexamined Patent Application Publication (Translation of PCT Application) No. 2007-527938
PTL 6: Japanese Unexamined Patent Application Publication No. 2008-303160
PTL 7: Japanese Unexamined Patent Application Publication No. 2009-29712
PTL 8: Japanese Unexamined Patent Application Publication No. 2009-51760
PTL 9: Japanese Unexamined Patent Application Publication No. 2009-167129
PTL 10: Japanese Unexamined Patent Application Publication No. 2009-167183
PTL 11: Japanese Unexamined Patent Application Publication No. 2009-173611
PTL 12: Japanese Unexamined Patent Application Publication No. 2009-220105

SUMMARY OF INVENTION

Technical Problem

An object of the present invention is to increase the yield of alcohols by a Guerbet reaction in a gas phase and reduce production cost.

Solution to Problem

As described in the above patent documents, a Guerbet reaction is generally performed under normal pressure and sometimes performed under increased pressure. Moreover, in actual plant engineering, it is common practice to perform the reaction under normal or increased pressure from the viewpoint of easy operability, reduction of production cost, and the like. For example, when the pressure in plant piping is increased, even if some slight leakage of raw materials or products from small gaps or cracks in the piping occurs, no effect is found on the catalyst and the product selectivity. However, if the pressure in piping around the plant reactor is reduced, entry of air into the piping from small gaps or cracks in piping joints or the like may occur, and if the entry of air occurs anterior to the reactor, oxidation can occur, depending on the raw materials, leading to reduction in product selectivity and yield, and the catalyst may be oxidized, depending on the catalyst, undergoing inactivation earlier than expected.

It is to be noted that according to Le Chatelier's principle, when a gas phase reaction is carried out under increased pressure the reaction adjusts itself so that pressure increase is minimized to reduce the number of molecules in the gas phase, whereas the opposite adjustment takes place under reduced pressure. More specifically, according to Le Chatelier's principle, in the case of a reaction involving 2 mol of raw materials and 1 mol of a product, as described below (Equation 1), a higher amount of "D" is produced by increasing pressure, whereas the reaction is resistant to progression under reduced pressure.

[Chem.1]

$$A+B \rightarrow D \qquad \text{(Equation 1)}$$

On the other hand, because the Guerbet reaction (Equation 2) is a reaction in which the number of moles does not change between the raw material and the products, the number of particles in a gas phase will not increase or decrease depending on the adjustment of reaction even if the pressure changes, and thus, the degree of conversion and yield are expected to be independent of pressure.

[Chem.2]

$$2C_2H_5OH \rightarrow C_4H_9OH+H_2O \qquad \text{(Equation 2)}$$

Under such circumstances, where no merit in performing a reaction at reduced pressure has been found, the present inventors ventured to perform a Guerbet reaction under reduced pressure, and surprisingly found that a high degree of conversion of raw material alcohol (yield) can be obtained, thereby accomplishing the present invention.

More specifically, the present invention relates to (1) a method for producing an alcohol by a Guerbet reaction, wherein the reaction is performed in a gas phase and at a total pressure of less than 1 atm, using one or more raw material alcohols, (2) the method for producing an alcohol according to (1) above, wherein the total pressure is 0.01 to 0.9 atm, (3) the method for producing an alcohol according to (1) above, wherein the total pressure is 0.01 to 0.8 atm, and (4) the method for producing an alcohol according to (1) above, wherein the total pressure is 0.01 to 0.5 atm.

In addition, the present invention relates to (5) the method for producing an alcohol according to any one of the above (1) to (4), wherein a basic catalyst is used, (6) the method for producing an alcohol according to (5) above, wherein the basic catalyst comprises an apatite structure compound, (7) the method for producing an alcohol according to (5) above, wherein the basic catalyst is one or more selected from calcium hydroxyapatite, strontium hydroxyapatite, hydrotalcite, MgO, $Mg(OH)_2$, and alkali metal supported-zeolite, (8) the method for producing an alcohol according to any one of the above (1) to (7), wherein the raw material alcohol comprises ethanol, (9) the method for producing an alcohol according to any one of the above (1) to (8), wherein the raw material alcohol is ethanol, and (10) the method for producing an alcohol according to (9) above, wherein the produced alcohol comprises 1-butanol.

Advantageous Effects of Invention

According to the method for producing alcohols in the present invention, the yield of alcohol from a Guerbet reaction can be increased, and the production cost can be reduced.

DESCRIPTION OF EMBODIMENTS

The method of the present invention is a method for producing alcohols by a Guerbet reaction and is not particularly limited so long as the method includes performing the reaction in a gas phase and at a total pressure of less than 1 atm, using one or more raw material alcohols. The method of the present invention is characterized by performing the reaction under an environment of a gas phase and a total pressure of less than 1 atm. Specifically, in the method of the present invention, it is preferred that one or more vaporized raw material alcohols be introduced into a reaction system and reacted at less than 1 atm.

The pressure (total pressure) of the reaction system may be less than 1 atm as described above. Since an inexpensive vacuum apparatus such as an oil-sealed rotary vacuum pump (rotary pump) can be used, the pressure is preferably 0.01 to 0.9 atm and more preferably 0.01 to 0.8 atm. In addition, the pressure is preferably 0.01 to 0.5 atm, from the viewpoint of obtaining a higher yield. A further reduction in the pressure allows the contact time (W/F) to be further shortened and the productivity to be increased. In addition, when 1-butanol is synthesized, a further reduction in the pressure allows the reaction temperature to be further lowered and the selectivity of 1-butanol to be increased.

The raw material alcohol may be a linear alcohol or a branched chain alcohol and may be a saturated alcohol or an unsaturated alcohol. Also, the number of carbon atoms thereof is not particularly limited and the raw material alcohol is preferably an alcohol having 1 to 22 carbon atoms and more preferably an alcohol having 1 to 8 carbon atoms, from the viewpoint of easy availability. Specifically, methanol, ethanol, 1-propanol, 1-butanol, 1-pentanol, 1-hexanol, 1-heptanol, and 1-octanol are preferable. In addition, as the raw material alcohol, at least one alcohol is preferably ethanol, and a Guerbet alcohol can be produced in a higher yield by using ethanol. Also, when only ethanol is used as the raw material alcohol, a linear alcohol having 4 or more and an even number of carbon atoms, such as 1-butanol, can be produced in a higher yield. The term Guerbet alcohols in the present application refers to alcohols produced by a Guerbet reaction.

When two raw material alcohols are used, the proportion of each alcohol used (mixing ratio) is not particularly limited, but in order to synthesize alcohols in a higher yield, when the degrees of conversion of the two raw material alcohols are about the same, the mixing ratios are preferably approximately equimolar (1:0.9 to 1.1 or so), and when the degrees of conversion of the two alcohols are different, it is preferred that more of the alcohols having a lower degree of conversion be mixed, so that the amounts converted are about the same.

In the method for producing alcohols according to the present invention, it is preferred to use a basic catalyst having basicity (base catalyst or acid-base catalyst). Examples of the basic catalyst can include apatite structure compounds, hydrotalcite compounds, MgO, Mg(OH)$_2$, alkali metal supported zeolite, kaolin clay minerals, pyrophyllite clay minerals, smectite clay minerals, calcium silicate, calcium fluoride, calcium sulfate, lithium phosphate, aluminum phosphate, magnesium phosphate, titanium oxide, calcium hydroxide, and sepiolite.

The above apatite structure compounds can be represented by a general formula $M_a(M'O_b)_cX_2$. M represents Ca, Sr, Mg, Ba, Pb, Cd, Fe, Co, Ni, Zn, H, or the like, and M' represents P, V, As, C, S, or the like, X represents OH, F, Cl, Br, or the like, and each may be one type or more types. $M_{10}(M'O_4)_6X_2$ wherein a is 10, b is 4, c is 6, and a/c is 1.67 is a fundamental apatite compound. In cases where the compound is a solid solution or where a/c deviates from 1.67, or where M comprises an element other than divalent elements, or where M' comprises an element other than pentavalent elements such as C and S, the chemical formula is different from that of the above fundamental apatite compound. a/c is generally between 1.5 and 1.8 but not limited thereto. When M, M', and X are a combination of two or more elements, a and c are each the total valence of the respective elements.

The above hydrotalcite compounds can be represented by a general formula $[M^{2+}_{1-x}M^{3+}_x(OH)_2]^{x+}[A^{n-}_{x/n} \cdot mH_2O]^{x-}$. $M^{2+}$ represents a divalent metal ion such as $Mg^{2+}$, $Fe^{2+}$, $Zn^{2+}$, $Ca^{2+}$, $Li^{2+}$, $Ni^{2+}$, $Co^{2+}$, $Pt^{2+}$, $Pd^{2+}$, and $Cu^{2+}$, $M^{3+}$ represents a trivalent metal ion such as $Al^{3+}$, $Fe^{3+}$, $Cr^{3+}$, and $Mn^{3+}$, $A^{n-}$ represents an n-valent anion such as $CO_3^{2-}$ and $OH^-$, and each may be one type or more types. m is a value of 0 or more, and x is generally between 0.2 and 0.4 but not limited thereto.

Among the above basic catalysts, calcium hydroxyapatite, wherein the above apatite structure compound contains Ca as M and P as M', strontium hydroxyapatite wherein it contains Sr as M and P as M', hydrotalcite, wherein the above hydrotalcite contains $Mg^{2+}$ as $M^{2+}$, $Al^{3+}$ as $M^{3+}$ and $CO_3^{2-}$ as $A^{n-}$, and MgO, Mg(OH)$_2$, and alkali metal supported zeolite are preferable, and calcium hydroxyapatite is particularly preferable. Examples of an alkali metal in the alkali metal supported zeolite can include specifically Li, Na, K, Rb, and Cs, and these may be used alone or may be used in combinations of two or more.

The above calcium hydroxyapatite is a calcium phosphate and stoichiometrically its composition is shown as $Ca_{10}(PO_4)_6(OH)_2$. Even if the composition is nonstoichiometrical indicating that the Ca/P molar ratio is not 1.67, it shows features of calcium hydroxyapatite and can take an apatite structure, and synthetic calcium hydroxyapatite having a Ca/P molar ratio of 1.4 to 1.8 or so is also included in the calcium hydroxyapatite in the present invention. In particular, in the method for producing alcohols according to the present invention, calcium hydroxyapatite having a Ca/P molar ratio of 1.60 to 1.80 is preferable. Calcium hydroxyapatite having any shape, whether a granule, a sphere, a pellet, a honeycomb, or the like, can be used. It should be noted that as described above, the calcium hydroxyapatite of the present invention includes a composition in which part of Ca is replaced with another metal.

The above strontium hydroxyapatite can be described as being obtained by replacing a calcium atom or atoms (Ca) of the above calcium hydroxyapatite with a strontium atom or atoms (Sr). In other words, the composition of the above strontium hydroxyapatite stoichiometrically is shown as $Sr_{10}(PO_4)_6(OH)_2$. Even if the composition is nonstoichiometrical indicating that the Sr/P molar ratio is not 1.67, it shows features of strontium hydroxyapatite and can take an apatite structure, and strontium hydroxyapatite having a Sr/P molar ratio of 1.4 to 1.8 or so is also included in the strontium hydroxyapatite in the present invention. As in the case of calcium hydroxyapatite, in the method for producing alcohols according to the present invention, strontium hydroxyapatite having a Sr/P molar ratio of 1.60 to 1.80 is preferable, and strontium hydroxyapatite having any shape, whether a granule, a sphere, a pellet, a honeycomb, or the like can be used. It should be noted that as described above, the strontium hydroxyapatite of the present invention includes a composition in which part of Sr is replaced with another metal.

In addition, the above hydrotalcite is a clay mineral having a composition shown by a general formula $[Mg_{1-x}Al_x(OH)_2]^{x+}[(CO_3)_{x/2}yH_2O]^{x-}$, and representative examples can include $Mg_6Al_2(OH)_{16}CO_34H_2O$, $Mg_{4.5}Al_2(OH)_{13}CO_3.5H_2O$, $Mg_{4.5}Al_2(OH)_{13}CO_3$, and $Mg_{4.3}Al_2(OH)_{12.6}CO_3.5H_2O$. A granule, a sphere, a pellet, a honeycomb, or the like can be used as the shape thereof, as in the case of calcium hydroxyapatite. It should be noted that as described above, the hydrotalcite of the present invention includes a composition in which part of Mg and/or Al is replaced with another metal.

Calcium hydroxyapatite, strontium hydroxyapatite, hydrotalcite, and the like may support or be substituted with a substance contributing to a Guerbet reaction, such as an alkali metal, a transition metal, or a noble metal as necessary. Examples of the substance contributing to a Guerbet reaction can include alkali metals, Ni, Zn, Cu, Pd, and Pt. In addition, for synergetic effect or increase in durability, a plurality of metals may be co-supported thereon. Examples of co-supported metals can include transition metals such as Zn, Co, Cr, Mo, W, Fe, Ni, Cu, Mn, Ti, V, Ga, Zr, Nb, Cd, In, Sn, Sb, Pb, La, Ce, Eu, and Y, noble metals such as Pt, Pd, Rh, Au, Ir, Ru, and Ag, and alkali or alkaline earth metals such as Ba, Na, K, Li, Sr, Ca, Mg, Cs, and Rb, and oxides or sulfides of these metals can be also used in some cases. It should be noted that alkali metal supported zeolite can also support a substance other than alkali metals.

As the method of supporting an alkali metal or the like, a conventional method generally used as a supporting method such as an ion exchange method, an impregnation method, and a physical mixing method can be used. In addition, when calcium hydroxyapatite or the like is synthesized, an alkali metal or the like may be made to coexist with it.

In the method of the present invention, a serial process is preferable from the viewpoint of industrial economic efficiency. In the introduction of gas into a reactor, the raw material alcohol gas may be introduced either alone or together with an inactive carrier gas such as nitrogen or helium, but according to the method of the present invention, even when raw material alcohol gas alone is introduced, Guerbet alcohol can be produced in high yield, and thus the method of the present invention is industrially advantageous. Namely, in a conventional method using a carrier gas, although the yield can be increased by suppressing unnecessary retention of the raw materials and products, there is a problem of increased production cost considering the price of the carrier gas, a treatment facility for reusing the carrier gas, the energy required for heating the carrier gas, and the like. On the other hand, the method of reducing pressure according to the present invention is feasible at lower cost than the costs that arise from using a carrier gas, and the effect on increasing yield is very high, and thus it is a very good method.

When two or more alcohols are subjected to a gas phase reaction, it is preferable to vaporize the alcohol mixture solution, and to vaporize it quickly without reacting the alcohols. Therefore, as a vaporization temperature, a temperature higher than the boiling point of the higher boiling alcohol, at which the lower boiling alcohol does not react, is preferable. Specifically, a preferable temperature is 150 to 200 deg C. in the case of methanol and ethanol, and 200 to 250 deg C. in the case of ethanol and 1-octanol. Or, alternatively, a reaction can be performed by first introducing one vaporized alcohol and then the other alcohol in gas form. When ethanol is used, it is preferred to introduce ethanol first before any other raw material gas.

In addition, while it depends on the degree of pressure reduction, the contact time (W/F) in the reaction of the present invention is preferably 0.01 to 200 h and more preferably 0.05 to 50 h. In addition, the reaction temperature is preferably 200 deg C. to 600 deg C. and more preferably 200 deg C. to 450 deg C.

EXAMPLE 1

Catalyst (1) Calcium Hydroxyapatite Catalyst

A calcium hydroxyapatite catalyst (CaHAP catalyst) was prepared by the precipitation method. Special grade reagents of Wako Pure Chemical Industries, Ltd. were used for all raw materials. The preparation procedure is as described below.

Using a 0.60 mol/l aqueous solution of calcium nitrate tetrahydrate adjusted to pH 10 with aqueous ammonia and a 0.40 mol/l aqueous solution of diammonium hydrogenphosphate adjusted to pH 10 with aqueous ammonia as starting materials, raw material solutions of which the solution feed rate was adjusted so as to synthesize calcium hydroxyapatite in a predetermined Ca/P molar ratio were each separately added dropwise to distilled water via a solution feed pump. After dropping predetermined amounts, the resulting substance was thoroughly stirred for 24 hours, filtered, washed with water, and dried at 140 deg C. Ion-exchanged water was added to the resulting powder to give a suspension at a calcium hydroxyapatite concentration of 10 wt %, and then, the suspension was matured and dried in a drier at 140 deg C. and ground in a mortar. Thereafter, the substance was calcined at 600 deg C. for 2 hours in the air, to obtain a powdered calcium hydroxyapatite catalyst.

The synthesized calcium hydroxyapatite catalyst was characterized by powder X-ray diffraction, and the specific surface area (BET) value was measured. The Ca/P molar ratio of the catalyst was obtained by fluorescent X-ray using the calibration curve method. Powder X-ray diffraction showed that each catalyst was constituted by a single phase of calcium hydroxyapatite. The specific surface area (BET) value was 46 $m^2/g$, and the Ca/P molar ratio was 1.67. For an alcohol conversion reaction, a substance of 14 to 26 mesh size obtained by forming the calcium hydroxyapatite powder into pellets with a tableting machine and slightly grinding the pellets was used.

(2) Hydrotalcite Catalyst

A substance of 14 to 26 mesh size obtained by forming a special grade reagent hydrotalcite catalyst of Wako Pure Chemical Industries, Ltd. into pellets with a tableting machine and slightly grinding the pellets was used.

(3) $Mg(OH)_2$ Catalyst

A substance of 14 to 26 mesh size obtained by boiling a MgO reagent of Wako Pure Chemical Industries, Ltd. in distilled water to hydrate it (refer to Ueda, W.; Kuwabara, T.; Ohshida, T.; Morikawa, Y. A Low-pressure Guerbet Reaction over Magnesium Oxide Catalyst. J. Chem. Soc., Chem. Commun., 1990, 1558-1559.), forming it into pellets with a tableting machine, and slightly grinding the pellets was used.

(4) Strontium Hydroxyapatite Catalyst

A strontium hydroxyapatite catalyst (SrHAP catalyst) was prepared by the precipitation method. Special grade reagents of Wako Pure Chemical Industries, Ltd. were used for all raw materials. The preparation procedure is as described below.

Using a 0.60 mol/l aqueous solution of strontium nitrate adjusted to pH 10 with aqueous ammonia and a 0.40 mol/l aqueous solution of diammonium hydrogenphosphate adjusted to pH 10 with aqueous ammonia as starting materials, raw material solutions of which the solution feed rate was adjusted so as to synthesize strontium hydroxyapatite in a predetermined Sr/P molar ratio were each separately added dropwise to distilled water via a solution feed pump. After dropping predetermined amounts, the resulting substance was thoroughly stirred for 24 hours, filtered, washed with water, and dried at 140 deg C. Ion-exchanged water was added to the resulting powder to give a suspension at a strontium hydroxyapatite concentration of 10 wt %, and then, the suspension was matured and dried in a drier at 140 deg C. and ground in a mortar. Thereafter, the substance was calcined at 600 deg C. for 2 hours in the air, to obtain a powdered strontium hydroxyapatite catalyst. For an alcohol conversion reaction, a substance of 14 to 26 mesh size obtained by forming the strontium hydroxyapatite powder into pellets with a tableting machine and slightly grinding the pellets was used.

(5) Rb—Li Ion-Substituted Zeolite Catalyst

A Rb—Li ion-substituted zeolite catalyst was prepared by an ion exchange treatment and impregnation method. Special grade reagents of Wako Pure Chemical Industries, Ltd. were used for all raw materials. The preparation procedure is as described below.

The ion exchange treatment of 13× zeolite was performed using a 0.5 mol/l lithium chloride aqueous solution heated to 80 deg C., to obtain a Li ion-exchanged zeolite, and this was impregnated with a rubidium nitrate aqueous solution, and calcined at 300 deg C. for 20 hours in the atmosphere, to obtain a Rb—Li ion-substituted zeolite catalyst. A substance of 14 to 26 mesh size obtained by slightly grinding this Rb—Li ion-substituted zeolite catalyst was used.

(Raw Materials)

As raw material ethanols, Wako Pure Chemical Industries, Ltd. special grade reagent ethanol (99.5), special grade reagent ethanol (95), and special grade reagent ethanol (99.5) adjusted to 70 vol % by adding distilled water were respectively used. In addition, as a methanol/ethanol mixed raw material, a mixture of special grade reagent methanol (99.8) and special grade reagent ethanol (99.5) prepared so as to have a molar ratio of 1:1 was used. Further, as an ethanol/1-propanol mixed raw material, a mixture of special grade reagent ethanol (99.5) and special grade reagent 1-propanol (99.5) prepared so as to have a molar ratio of 1:1 was used.

(Experiment)

A fixed-bed gas flow catalytic reactor (manufactured by Ohkura Riken Co., Ltd.) capable of setting pressure reduction conditions was used as a reactor. A SUS reaction tube was filled with a predetermined amount of the catalyst, and a raw material gas (100 vol %) was introduced thereinto, to react them at the pressure (atm), W/F [$g_{CAT}/(g_{Ethanol}/h)$], and reaction temperature (deg C) shown in the tables below. The control of reaction pressure was performed using a vacuum pump while monitoring pressure with pressure gauges located in the inlet and outlet of the reactor. In addition, using an online gas chromatograph (GC) (detector: FID) to measure the degree of conversion of the alcohol and the yield and selectivity of the synthesized gas, the amount of each component was determined from the peak area of the component. The results are shown in Tables 1 to 14. The target product Guerbet alcohols of Examples D to F are each a mixture of alcohols having 4, 6, 8, 10, and 12 carbon atoms.

In addition, the reaction product yield was obtained by the following formula:

$$\text{Reaction product yield } (C\text{-wt \%}) = (\text{Number of moles of carbon of each product/Total number of moles of carbon}) \times 100$$

TABLE 1

Synthesis of 1-Butanol from 100 vol % Ethanol with CaHAP Catalyst (W/F 10 h)

| | Comparative Example A-0 | Comparative Example A-1 | Comparative Example A-2 | Example A-3 | Example A-4 | Example A-5 | Example A-6 | Example A-7 |
|---|---|---|---|---|---|---|---|---|
| Reaction Pressure/atm | 5.0 | 2.0 | 1.0 | 0.90 | 0.80 | 0.50 | 0.20 | 0.050 |
| Set Temperature/° C. | | | | 1-Butanol Yield/C-wt % | | | | |
| 200 | 0.0 | 0.0 | 0.1 | 0.2 | 0.3 | 0.4 | 0.8 | 1.2 |
| 225 | 0.3 | 0.5 | 0.9 | 1.0 | 1.2 | 1.6 | 3.9 | 13.8 |
| 250 | 1.4 | 4.0 | 8.3 | 8.9 | 10.2 | 13.6 | 22.1 | 32.6 |

TABLE 2

Synthesis of 1-Butanol from 100 vol % Ethanol with CaHAP Catalyst (W/F 1 h)

| | Comparative Example B-0 | Comparative Example B-1 | Comparative Example B-2 | Example B-3 | Example B-4 | Example B-5 | Example B-6 | Example B-7 |
|---|---|---|---|---|---|---|---|---|
| Reaction Pressure/atm | 5.0 | 2.0 | 1.0 | 0.90 | 0.80 | 0.50 | 0.20 | 0.050 |

TABLE 2-continued

Synthesis of 1-Butanol from 100 vol % Ethanol with CaHAP Catalyst
(W/F 1 h)

| Set Temperature/ °C. | Comparative Example B-0 | Comparative Example B-1 | Comparative Example B-2 | Example B-3 | Example B-4 | Example B-5 | Example B-6 | Example B-7 |
|---|---|---|---|---|---|---|---|---|
| | | | | 1-Butanol Yield/C-wt % | | | | |
| 250 | 1.1 | 1.6 | 3.7 | 4.4 | 5.0 | 6.7 | 9.9 | 13.1 |
| 275 | 6.0 | 8.8 | 12.7 | 13.2 | 13.8 | 16.4 | 20.8 | 23.4 |
| 300 | 12.8 | 15.4 | 19.3 | 19.4 | 19.5 | 21.0 | 24.0 | 25.3 |
| 325 | 16.2 | 18.7 | 21.9 | 22.2 | 22.7 | 24.0 | 26.1 | 26.9 |
| 350 | 18.0 | 22.2 | 26.2 | 26.4 | 26.5 | 26.9 | 28.8 | 30.1 |

TABLE 3

Synthesis of 1-Butanol from 100 vol % Ethanol with CaHAP Catalyst
(W/F 0.1 h)

| | Comparative Example C-0 | Comparative Example C-1 | Comparative Example C-2 | Example C-3 | Example C-4 | Example C-5 |
|---|---|---|---|---|---|---|
| Reaction Pressure/atm | 5.0 | 2.0 | 1.0 | 0.50 | 0.20 | 0.050 |
| Set Temperature/ °C. | | | 1-Butanol Yield/C-wt % | | | |
| 350 | 1.4 | 2.1 | 4.0 | 5.7 | 7.0 | 7.4 |
| 375 | 3.7 | 4.0 | 5.9 | 8.3 | 9.8 | 10.0 |
| 400 | 6.4 | 6.8 | 8.3 | 11.9 | 15.1 | 16.0 |
| 425 | 7.2 | 8.4 | 9.9 | 14.8 | 18.4 | 19.2 |
| 450 | 7.8 | 8.9 | 10.5 | 15.6 | 19.1 | 20.4 |

TABLE 4

Synthesis of Guerbet Alcohol from 100 vol % Ethanol with CaHAP Catalyst
(W/F 10 h)

| | Comparative Example D-0 | Comparative Example D-1 | Comparative Example D-2 | Example D-3 | Example D-4 | Example D-5 | Example D-6 | Example D-7 |
|---|---|---|---|---|---|---|---|---|
| Reaction Pressure/atm | 5.0 | 2.0 | 1.0 | 0.90 | 0.80 | 0.50 | 0.20 | 0.050 |
| Set Temperature/ °C. | | | | Alcohol Yield/C-wt % | | | | |
| 200 | 0.0 | 0.0 | 0.1 | 0.2 | 0.3 | 0.4 | 0.8 | 1.3 |
| 225 | 0.3 | 0.6 | 0.9 | 1.1 | 1.3 | 1.7 | 4.2 | 15.5 |
| 250 | 1.5 | 4.2 | 8.8 | 9.4 | 10.7 | 14.6 | 27.7 | 57.9 |

TABLE 5

Synthesis of Guerbet Alcohol from 100 vol % Ethanol with CaHAP Catalyst
(W/F 1 h)

| | Comparative Example E-0 | Comparative Example E-1 | Comparative Example E-2 | Example E-3 | Example E-4 | Example E-5 | Example E-6 | Example E-7 |
|---|---|---|---|---|---|---|---|---|
| Reaction Pressure/atm | 5.0 | 2.0 | 1.0 | 0.90 | 0.80 | 0.50 | 0.20 | 0.050 |

TABLE 5-continued

Synthesis of Guerbet Alcohol from 100 vol % Ethanol with CaHAP Catalyst
(W/F 1 h)

| | Comparative Example E-0 | Comparative Example E-1 | Comparative Example E-2 | Example E-3 | Example E-4 | Example E-5 | Example E-6 | Example E-7 |
|---|---|---|---|---|---|---|---|---|
| Set Temperature/°C. | | | | Alcohol Yield/C-wt % | | | | |
| 250 | 1.1 | 1.8 | 4.1 | 4.9 | 5.7 | 7.9 | 11.9 | 21.9 |
| 275 | 6.6 | 10.3 | 14.9 | 16.0 | 17.2 | 20.2 | 30.6 | 40.4 |
| 300 | 15.4 | 19.9 | 25.0 | 25.6 | 26.3 | 30.5 | 36.4 | 43.3 |
| 325 | 19.9 | 26.4 | 30.9 | 31.4 | 32.1 | 35.4 | 38.8 | 44.6 |
| 350 | 22.9 | 35.5 | 41.9 | 42.1 | 42.2 | 45.0 | 47.2 | 49.8 |

TABLE 6

Synthesis of Guerbet Alcohol from 100 vol % Ethanol with CaHAP Catalyst
(W/F 0.1 h)

| | Comparative Example F-0 | Comparative Example F-1 | Comparative Example F-2 | Example F-3 | Example F-4 | Example F-5 |
|---|---|---|---|---|---|---|
| Reaction Pressure/atm | 5.0 | 2.0 | 1.0 | 0.50 | 0.20 | 0.050 |
| Set Temperature/°C. | | | Alcohol Yield/C-wt % | | | |
| 350 | 1.5 | 2.3 | 4.4 | 6.1 | 8.0 | 8.8 |
| 375 | 4.5 | 4.8 | 7.1 | 8.9 | 11.2 | 12.4 |
| 400 | 8.2 | 8.7 | 10.6 | 13.2 | 19.8 | 20.8 |
| 425 | 12.3 | 14.3 | 16.8 | 21.4 | 28.1 | 30.1 |
| 450 | 13.5 | 15.4 | 18.1 | 23.8 | 30.7 | 32.4 |

TABLE 7

Synthesis of 1-Butanol from 95 vol % Ethanol with CaHAP Catalyst
(W/F 2.7 h)

| | Comparative Example G-0 | Comparative Example G-1 | Comparative Example G-2 | Example G-3 | Example G-4 | Example G-5 |
|---|---|---|---|---|---|---|
| Reaction Pressure/atm | 5.0 | 2.0 | 1.0 | 0.50 | 0.20 | 0.050 |
| Set Temperature/°C. | | | 1-Butanol Yield/C-wt % | | | |
| 250 | 0.3 | 0.8 | 1.6 | 3.1 | 5.0 | 6.1 |
| 275 | 4.9 | 6.2 | 8.1 | 12.3 | 15.5 | 17.1 |
| 300 | 10.1 | 12.4 | 15.8 | 17.8 | 21.0 | 22.4 |
| 325 | 10.8 | 13.6 | 17.9 | 20.6 | 22.6 | 24.1 |
| 350 | 14.6 | 18.1 | 22.7 | 24.7 | 26.0 | 26.6 |

TABLE 8

Synthesis of 1-Butanol from 70 vol % Ethanol with CaHAP Catalyst
(W/F 2.7 h)

| | Comparative Example H-0 | Comparative Example H-1 | Comparative Example H-2 | Example H-3 | Example H-4 | Example H-5 |
|---|---|---|---|---|---|---|
| Reaction Pressure/atm | 5.0 | 2.0 | 1.0 | 0.50 | 0.20 | 0.050 |
| Set Temperature/°C. | | | 1-Butanol Yield/C-wt % | | | |
| 250 | 0.1 | 0.3 | 0.6 | 1.1 | 2.4 | 3.2 |
| 275 | 1.1 | 1.6 | 3.1 | 5.4 | 7.6 | 8.4 |
| 300 | 5.0 | 7.8 | 10.3 | 12.3 | 14.8 | 16.3 |
| 325 | 8.0 | 11.2 | 14.1 | 16.1 | 18.4 | 19.7 |
| 350 | 12.8 | 15.4 | 20.1 | 21.8 | 23.9 | 25.1 |

TABLE 9

Synthesis of 1-Butanol from 100 vol % Ethanol with Hydrotalcite Catalyst
(W/F 5.1 h)

| | Comparative Example I-0 | Comparative Example I-1 | Comparative Example I-2 | Example I-3 | Example I-4 | Example I-5 |
|---|---|---|---|---|---|---|
| Reaction Pressure/atm | 5.0 | 2.0 | 1.0 | 0.50 | 0.20 | 0.050 |
| Set Temperature/°C. | | | 1-Butanol Yield/C-wt % | | | |
| 200 | 0.0 | 0.0 | 0.0 | 0.1 | 0.1 | 0.2 |
| 225 | 0.1 | 0.3 | 0.4 | 0.5 | 0.7 | 1.1 |
| 250 | 2.1 | 2.9 | 3.5 | 5.3 | 7.2 | 8.4 |
| 275 | 4.7 | 6.1 | 8.9 | 13.1 | 17.6 | 19.8 |

TABLE 10

Synthesis of 1-Butanol from 100 vol % Ethanol with Mg(OH)$_2$ Catalyst
(W/F 9.8 h)

| | Comparative Example J-0 | Comparative Example J-1 | Comparative Example J-2 | Example J-3 | Example J-4 | Example J-5 |
|---|---|---|---|---|---|---|
| Reaction Pressure/atm | 5.0 | 2.0 | 1.0 | 0.50 | 0.20 | 0.050 |

TABLE 10-continued

Synthesis of 1-Butanol from 100 vol % Ethanol with Mg(OH)$_2$ Catalyst
(W/F 9.8 h)

| | Comparative Example J-0 | Comparative Example J-1 | Comparative Example J-2 | Example J-3 | Example J-4 | Example J-5 |
|---|---|---|---|---|---|---|
| Set Temperature/°C. | | | 1-Butanol Yield/C-wt % | | | |
| 250 | 0.0 | 0.0 | 0.0 | 0.0 | 0.1 | 0.2 |
| 275 | 0.1 | 0.2 | 0.3 | 0.6 | 1.0 | 1.4 |
| 300 | 2.7 | 3.1 | 3.8 | 5.0 | 6.5 | 7.4 |
| 325 | 5.5 | 6.8 | 8.7 | 10.1 | 12.2 | 13.9 |

TABLE 11

Synthesis of 1-Butanol from 100 vol % Ethanol with SrHAP Catalyst
(W/F 39 h)

| | Comparative Example K-0 | Comparative Example K-1 | Comparative Example K-2 | Example K-3 | Example K-4 | Example K-5 |
|---|---|---|---|---|---|---|
| Reaction Pressure/atm | 5.0 | 2.0 | 1.0 | 0.50 | 0.20 | 0.050 |
| Set Temperature/°C. | | | 1-Butanol Yield/C-wt % | | | |
| 200 | 0.0 | 0.1 | 0.2 | 0.3 | 0.3 | 0.6 |
| 225 | 0.8 | 1.1 | 1.3 | 1.4 | 2.1 | 4.8 |
| 250 | 12.4 | 14.7 | 17.6 | 21.8 | 30.4 | 37.0 |

TABLE 12

Synthesis of 1-Butanol from 100 vol % Ethanol with Rb—Li
Ion-substituted Zeolite Catalyst
(W/F 10 h)

| | Comparative Example L-0 | Comparative Example L-1 | Comparative Example L-2 | Example L-3 | Example L-4 | Example L-5 |
|---|---|---|---|---|---|---|
| Reaction Pressure/atm | 5.0 | 2.0 | 1.0 | 0.50 | 0.20 | 0.050 |
| Set Temperature/°C. | | | 1-Butanol Yield/C-wt % | | | |
| 225 | 0.3 | 0.4 | 0.4 | 0.9 | 1.4 | 2.2 |
| 250 | 2.3 | 3.3 | 5.1 | 6.2 | 7.5 | 9.2 |
| 275 | 5.5 | 7.1 | 8.5 | 9.7 | 11.1 | 12.1 |

TABLE 13

Synthesis of 1-Propanol from Methanol/Ethanol Mixture
Solution with CaHAP Catalyst
(W/F 10 h)

| | Comparative Example M-0 | Comparative Example M-1 | Comparative Example M-2 | Example M-3 | Example M-4 | Example M-5 |
|---|---|---|---|---|---|---|
| Reaction Pressure/atm | 5.0 | 2.0 | 1.0 | 0.50 | 0.20 | 0.050 |
| Set Temperature/°C. | | | 1-Propanol Yield/C-wt % | | | |
| 225 | 0.2 | 0.3 | 0.4 | 0.4 | 0.5 | 0.7 |
| 250 | 1.0 | 1.1 | 1.3 | 1.4 | 1.6 | 1.8 |
| 275 | 3.0 | 3.2 | 3.7 | 4.1 | 4.5 | 4.9 |
| 300 | 4.8 | 5.0 | 5.7 | 6.4 | 7.1 | 7.4 |
| 325 | 5.1 | 5.4 | 5.9 | 6.6 | 7.3 | 7.8 |

TABLE 14

Synthesis of 1-Pentanol from Ethanol/1-Propanol Mixture
Solution with CaHAP Catalyst
(W/F 7.9 h)

| | Comparative Example N-0 | Comparative Example N-1 | Comparative Example N-2 | Example N-3 | Example N-4 | Example N-5 |
|---|---|---|---|---|---|---|
| Reaction Pressure/atm | 5.0 | 2.0 | 1.0 | 0.50 | 0.20 | 0.050 |
| Set Temperature/°C. | | | 1-Pentanol Yield/C-wt % | | | |
| 250 | 0.1 | 0.1 | 0.3 | 0.4 | 0.5 | 0.7 |
| 275 | 1.0 | 1.2 | 1.4 | 1.5 | 1.7 | 2.1 |
| 300 | 2.2 | 2.6 | 3.1 | 3.8 | 4.5 | 4.9 |
| 325 | 3.3 | 3.7 | 4.5 | 5.6 | 6.3 | 6.8 |
| 350 | 3.9 | 4.4 | 5.1 | 6.3 | 7.0 | 7.6 |

Industrial Applicability

The Guerbet alcohols obtained by the production method of the present invention can be used as chemical industrial raw materials or a high octane fuel.

The invention claimed is:

1. A method for producing an alcohol by a Guerbet reaction, wherein the reaction is performed with the use of a basic catalyst in a gas phase and at a total pressure of 0.01 to 0.5 atm, using one or more raw material alcohols, wherein the basic catalyst comprises an apatite structure compound.

2. The method for producing an alcohol according to claim 1, wherein the basic catalyst is one or two selected from calcium hydroxyapatite and strontium hydroxyapatite.

3. The method for producing an alcohol according to claim 1, wherein the raw material alcohol comprises ethanol.

4. The method for producing an alcohol according to claim 1, wherein the raw material alcohol is ethanol.

5. The method for producing an alcohol according to claim 4, wherein the produced alcohol comprises 1-butanol.

6. The method for producing an alcohol according to claim 3, wherein the produced alcohol comprises 1-butanol.

7. A method for producing an alcohol by a Guerbet reaction, wherein the reaction is performed with the use of a basic catalyst in gas phase and at a total pressure of 0.01 to 0.5 atm, using one or more raw material alcohols, wherein the basic catalyst is one or more selected from hydrotalcite, MgO, and alkali supported-zeolite.

8. The method for producing an alcohol according to claim 7, wherein the raw material alcohol comprises ethanol.

9. The method for producing an alcohol according to claim 7, wherein the raw material alcohol is ethanol.

10. The method for producing an alcohol according to claim 8, wherein the produced alcohol comprises 1-butanol.

11. The method for producing an alcohol according to claim 9, wherein the produced alcohol comprises 1-butanol.

* * * * *

UNITED STATES PATENT AND TRADEMARK OFFICE
CERTIFICATE OF CORRECTION

| | | |
|---|---|---|
| PATENT NO. | : 9,056,811 B2 | |
| APPLICATION NO. | : 13/822047 | |
| DATED | : June 16, 2015 | |
| INVENTOR(S) | : Yoshioka et al. | |

It is certified that error appears in the above-identified patent and that said Letters Patent is hereby corrected as shown below:

In the claims:

Column 14, line 64, claim 7 should read:

--catalyst in a gas phase--;

Column 14, line 67, claim 7 should read:

--alkali metal supported-zeolite.--.

Signed and Sealed this
Twenty-second Day of December, 2015

Michelle K. Lee
*Director of the United States Patent and Trademark Office*